(12) United States Patent
Ikami et al.

(10) Patent No.: US 8,658,989 B2
(45) Date of Patent: Feb. 25, 2014

(54) FLUOROMETRIC ASSAY APPARATUS AND FLUOROMETRIC ASSAY METHOD

(75) Inventors: Seishi Ikami, Kanagawa (JP); Kazuhiro Makino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 2 days.

(21) Appl. No.: 13/478,958

(22) Filed: May 23, 2012

(65) Prior Publication Data

US 2012/0298885 A1   Nov. 29, 2012

(30) Foreign Application Priority Data

May 26, 2011 (JP) ................................. 2011-117870

(51) Int. Cl.
*G01V 8/00* (2006.01)
(52) U.S. Cl.
USPC ....................................................... 250/459.1
(58) Field of Classification Search
USPC ....................................................... 250/459.1
See application file for complete search history.

(56) References Cited

U.S. PATENT DOCUMENTS

| | | | |
|---|---|---|---|
| 6,241,948 B1 | 6/2001 | Watkins et al. | |
| 6,852,986 B1 * | 2/2005 | Lee et al. | 250/458.1 |
| 6,995,841 B2 * | 2/2006 | Scott et al. | 356/318 |
| 8,581,269 B2 * | 11/2013 | Kuk et al. | 257/88 |
| 2004/0178370 A1 | 9/2004 | Oldham et al. | |
| 2009/0230323 A1 * | 9/2009 | Lee et al. | 250/459.1 |
| 2009/0275113 A1 | 11/2009 | Maltezos et al. | |
| 2010/0105035 A1 * | 4/2010 | Hashsham et al. | 435/6 |
| 2010/0193705 A1 * | 8/2010 | Rasnow et al. | 250/459.1 |
| 2011/0168918 A1 * | 7/2011 | Wimberger-Friedl et al. | 250/459.1 |

FOREIGN PATENT DOCUMENTS

| | | |
|---|---|---|
| JP | 05-150164 A | 6/1993 |
| JP | 05-232042 A | 9/1993 |
| JP | 2001-083090 A | 3/2001 |
| JP | 2004-012702 A | 1/2004 |
| JP | 2004-347394 A | 12/2004 |
| JP | 2005-172614 A | 6/2005 |
| JP | 2005-283322 A | 10/2005 |
| JP | 2007-003323 A | 1/2007 |
| JP | 2008-100064 A | 5/2008 |
| JP | 2008-145405 A | 6/2008 |
| JP | 2009-300356 A | 12/2009 |
| JP | 2010-085152 A | 4/2010 |
| JP | 2010-091456 A | 4/2010 |
| WO | WO-98/05253 A1 | 2/1998 |
| WO | WO 02/093144 A1 | 11/2002 |

* cited by examiner

*Primary Examiner* — David Porta
*Assistant Examiner* — Djura Malevic
(74) *Attorney, Agent, or Firm* — Jean C. Edwards; Edwards Neils PLLC

(57) ABSTRACT

A fluorometric assay apparatus comprising an LED light source configured with at least two types of excitation LED that have different principle wavelengths from each other and are disposed in a two dimensional array on a substrate; an imaging lens for imaging a subject; a single excitation filter provided between the LED light source and a subject, the single excitation filter transmitting each of principle wavelength components of the LED light source; and a single detection long pass filter provided between the imaging lens and the subject.

9 Claims, 10 Drawing Sheets

FLUOROMETRIC ASSAY APPARATUS AND FLUOROMETRIC ASSAY METHOD

CROSS-REFERENCE TO RELATED APPLICATION

This application claims priority under 35 USC 119 from Japanese Patent Application No. 2011-117870 filed on May 26, 2011, the disclosure of which is incorporated by reference herein.

BACKGROUND OF THE INVENTION

1. Technical Field

The present invention is related to a fluorometric assay apparatus and a fluorometric assay method, and in particular to a fluorometric assay apparatus and fluorometric assay method employing as a light source plural types of LED for generating ultraviolet radiation and visible light.

2. Related Art

In fields of biochemistry, for example as described in Japanese Patent Laid-Open No. 2005-283322, imaging devices are proposed that capture images of subjects such as fluorescent light-emitting specimens marked with fluorescent stains that emit fluorescent light on being illuminated with excitation light or chemical light-emitting specimens that have been placed in contact with a chemical light-emitting substrate and emit light.

Products for such fields are available with highly monochromatic near infrared, red, green, blue, ultraviolet, and white light sources. Such products can cause light of each desired color to be emitted under control from computer software, and are capable of mechanically switching between each light source.

In such cases, for example with fluorescent stains EtBr (ethidium bromide) and SYBR Green (SYBR is a registered trade mark of Molecular Probe Inc., same is applied hereinafter), when both are respectively appropriately excited and detected, an excitation light source appropriate to the absorption characteristics of each stain is respectively selected and employed. This means that there is a requirement to appropriately select light sources such as an ultraviolet light source for EtBr and a blue light source for SYBR Green.

Namely, generally a light source unit is built with a light source and a first filter (excitation filter) placed directly after the light source. However an imaging technician needs to perform operations to switch over light source units in order to use a light source and first filter with spectral characteristics optimized to the specific fluorescent stain that was selected by the imaging technician. A second filter (detection filter) is further disposed immediately in front of an image pick-up element, and the excitation wavelength component is cut out so that excitation light is not incident on the image pick-up element.

As detection apparatuses capable of handling both EtBr and SYBR Green (for example Bio-Rad ChemiDoc) employing an ultraviolet fluorescent lamp that emits a main light band of wavelengths capable of exciting both EtBr and SYBR Green are known.

As described in for example JP-A No. 2008-145405, configurations exist that simultaneously illuminate excitation light of two different wavelengths as an excitation light source.

As described in for example JP-A No. 2005-172614, configurations exist that include LEDs that emit blue light and LEDs that emit ultraviolet light arrayed in a staggered grid pattern as a light source.

As described in JP-A No. 2009-300356, configurations exist in which two excitation light sources are caused to be illuminated intermittently at different frequencies, and in which corresponding fluorescent light is detected.

As described in JP-A No. 2010-091456, configurations exist that include LED light sources disposed in a regular pattern on a substrate configured such that light intensity can be controlled independently.

As described in JP-A No. 2001-083090, configurations exist that include, as excitation light sources, plural LED light sources disposed in a regular pattern on a substrate, configured such that the light intensity and the light emission wavelength of the excitation light from the plural LED light sources can be controlled independently.

However, in systems using an ultraviolet fluorescent light lamp that emits a main light band of wavelengths capable of exciting both EtBr and SYBR Green, the excitation efficiency with respect to the fluorescent stain SYBR Green is far from high, and as well as the shortcoming of heat generated by the light source affecting the specimen, there are also disadvantages with respect to compact design.

In the configuration of JP-A No. 2008-145405, since the way the excitation light hits specimens varies depending on the attachment positions of each of the light sources, it is not possible for each wavelength to illuminate equally, and effort is also required to prepare appropriate excitation filters for each light source and to switch them over as required.

In the configuration of JP-A No. 2005-172614, it is necessary to switch over detection filters on the detector side in order to obtain images for each wavelength, and also, as this configuration does not specifically employ fluorescent stains, there is no concept of cutting out or passing excitation light using filters.

In the configuration of JP-A No. 2009-300356, a high cost dichroic filter (interference filter) is used as an excitation light filter in order to illuminate a specimen with two excitation light sources along the same axis, and it is not possible to use a single excitation light filter for plural excitation light sources.

In the configuration of JP-A No. 2010-091456, it is necessary to prepare fluorescent light filters for each fluorescent stain in order for fluorescent light of different wavelength bands depending on each fluorescent stain to be transmitted. As well as an increase in the number and types of filter, there is also the shortcoming of the effort for switching over filters.

In the configuration of JP-A No. 2001-083090, configuration is for a light source for a microtiter plate furnished with plural hollows in for example a glass plate, with one LED employed per hollow (well), such that plural filters need to be provided in order to filter excitation light independently of each other. This also has the disadvantage of an increase in the number and types of filter, and the effort for switching over filters.

Operations to switch the light source unit over according to the fluorescent stain used, as described above, force an unnecessary burden on an operator (imaging technician).

SUMMARY

In consideration of the above circumstances, a subject of the present invention is to provide a lower cost fluorometric assay apparatus provided with a light source and excitation filter for exciting plural types of fluorescent stain without switching over filters, and a single long pass filter for detection, and provide a fluorometric assay method of the same.

The present invention uses a light source with spectral characteristics that has emission distributions for both ultraviolet and blue so as to be capable of illuminating in both an ultraviolet region and a blue region (this may possibly be achieved by a combination of plural light sources rather than a single light source). Then as an excitation filter, for example a single band pass filter that cuts out wavelengths shorter than 300 nm and longer than 500 nm, and allows wavelengths of 300 to 500 nm to pass is disposed over the light source. Then as a detection filter (fluorescent light filter), a single filter that allows wavelengths of 520 nm or longer to pass and cuts out shorter wavelengths is disposed alone in front of an imaging lens.

The fluorescent light emitted by EtBr is orange light of 500 nm or longer, with a peak in the vicinity of 590 nm, and the fluorescent light emitted by SYBR Green is green light of 490 nm or longer with a peak in the vicinity of 530 nm. Therefore ranges of wavelengths which are contained in the light from the light source and within the same ranges as the above mentioned fluorescent emission light are removed by the band pass filter, and only the fluorescent light emitted by the fluorescent stains is extracted. Further, only the fluorescent emission light is incident on the lens since excitation light within an ultraviolet region and a blue region is removed by the detection filter.

An operator (imaging technician) can consequently perform the correct procedures whichever of the fluorescent stains is employed without performing any operation to switch over light source units or filters. In other word, the operator does not need to be aware of which fluorescent stain is being employed.

A first aspect of the present invention is a fluorometric assay apparatus including: an LED light source configured with at least two types of excitation LED that have different principle wavelengths from each other and are disposed in a two dimensional array on a substrate; an imaging lens for imaging a subject; a single excitation filter provided between the LED light source and the subject, the single excitation filter transmitting each of principle wavelength components of the LED light source; and a single detection long pass filter provided between the imaging lens and the subject.

According to the first aspect, by configuring such that light illuminated from at least two types of LED disposed in a two dimensional array on a substrate is transmitted through a single excitation filter, the burden on an operator to switch over excitation filters or light source sections is eliminated, enabling plural fluorescent stains to be excited at lower cost. The number of manufacturing processes can also be reduced since there is no requirement to precisely match the illumination light intensity and directionality of each of the LEDs. Multi-stain fluorescent light detection at lower cost is also enabled by employing a single long pass filter in detection.

A second aspect of the present invention is the configuration of the first aspect wherein the detection long pass filter is an orange tinted transparent acrylic board that cuts out light having wavelengths of 520 nm or shorter.

According to the second aspect, multi-stain fluorescent light detection at lower cost is enabled by employing a low cost tinted acrylic board in detection.

A third aspect of the present invention is the configuration of the first or the second aspect wherein: the at least two types of LED include a near ultraviolet LED with a principle wavelength component of 312 nm or 365 nm and a blue LED with a principle wavelength component of 470 nm; and the single excitation filter is a band pass filter that transmits light of a band from near ultraviolet to blue.

According to the third aspect, since for example the typical fluorescent stain EtBr can be excited by the near ultraviolet LED, and SYBR Green can be can be excited by the blue LED, each type of fluorescent stain can be detected either separately or at the same time as each other.

A fourth aspect of the present invention is the configuration of the third aspect wherein the LED light source is configured by a two dimensional array disposed on a substrate such that the number of individual near ultraviolet LEDs per unit surface area increases as the separation distance from the subject gets shorter.

According to the fourth aspect, since configuration is made with the two dimensional array disposed on a subject such that the number of individual near ultraviolet LEDs increases as the separation distance from the subject gets shorter, it is possible to increase the illumination intensity on the surface of the subject for the ultraviolet light which generally has a lower intensity than visible light, and thereby increase sensitivity.

A fifth aspect of the present invention is the configuration of the third aspect or the fourth aspect wherein the band pass filter cuts out light having wavelengths of 300 nm or shorter and cuts out light having wavelengths of 500 nm or longer and has a transmission peak in the vicinity of 400 nm.

According to the fifth aspect, since for example the typical fluorescent stain EtBr can be excited by light with wavelengths more than 300 and less than 500 nm, and SYBR Green can be excited by light including a peak wavelength in the vicinity of 370 nm, each type of fluorescent stain can be detected either separately or at the same time as each other.

A sixth aspect of the present invention is the configuration of the third aspect or the fourth aspect wherein the band pass filter cuts out light having wavelengths of 260 nm or shorter and cuts out light having wavelengths of 400 nm or longer and has a transmission peak in the vicinity of 330 nm.

According to the sixth aspect, since for example the typical fluorescent stain EtBr can be excited by light with wavelengths of 300 to 400 nm, and SYBR Green can be excited by light including a peak wavelength in the vicinity of 300 nm, each type of fluorescent stain can be detected either separately or at the same time as each other.

A seventh aspect of the present invention is a fluorometric assay method including: exciting at least two types of fluorescent light emitting substance provided at a subject with a light source section configured with at least two types of excitation LED and a single excitation filter. The at least two types of fluorescent light emitting substance have different maximum absorption wavelengths to each other. The at least two types of excitation LED have different principle wavelengths from each other and are disposed in a two dimensional array on a substrate. The single excitation filter covers the LEDs and transmits each of the principle wavelength components of the at least two types of excitation LED. The method further includes detecting fluorescent emission light that has been given off by the fluorescent light emitting substances and has passed through a single long pass filter provided as a detection filter between an imaging lens and the subject.

According to the seventh aspect, since light emitted from at least two types of LED disposed in a two dimensional array on a substrate is employed as excitation light that passes through a single excitation filter, the burden on an operator to switch over excitation filters or light source sections is eliminated, enabling plural fluorescent stains to be excited at lower cost. Regulation is also simplified since differences in illumination intensity and directionality between each of the LEDs do not tend to have much of an impact. Multi-stain fluorescent light detection at lower cost is also enabled by employing a single long pass filter for detection.

An eighth aspect of the present invention is the configuration of the seventh aspect wherein the fluorescent light emitting substances are stained with EtBr and SYBR Green.

According to the eighth aspect, a typical fluorescent stain such as EtBr having an absorption band in an ultraviolet region, and a typical fluorescent stain such as SYBR Green having an absorption band in a blue region can be detected either separately or at the same time as each other.

A ninth aspect of the present invention is the configuration of the seventh aspect wherein the fluorescent light emitting substances are stained with EtBr and SYBR Safe.

According to the ninth aspect, a typical fluorescent stain such as EtBr having an absorption band in an ultraviolet region, and a typical fluorescent stain such as SYBR Safe having an absorption band in a blue region can be detected either separately or at the same time as each other.

A tenth aspect of the present invention is the configuration of the seventh aspect wherein the fluorescent light emitting substances are stained with EtBr and SYBR Gold.

According to the tenth aspect, a typical fluorescent stain such as EtBr having an absorption band in an ultraviolet region, and a typical fluorescent stain such as SYBR Gold having an absorption band in a blue region can be detected either separately or at the same time as each other.

An eleventh aspect of the present invention is the configuration of the seventh aspect wherein the at least two types of excitation LED with different principle wavelengths emit light at the same time as each other. According to the eleventh aspect, the burden of switching excitation filters or light source sections becomes unnecessary, and plural fluorescent stain excitation at lower cost is enabled.

By configuring the present invention as described above, a lower cost fluorometric assay apparatus provided with a light source and an excitation filter for exciting plural types of fluorescent stain without switching over filters, and with a single long pass filter for detection, and a fluorometric assay method of the same can be achieved.

DETAILED DESCRIPTION OF THE INVENTION

Relevant Portions

Explanation follows regarding an exemplary embodiment of the present invention, with reference to the drawings.

Figure 1:
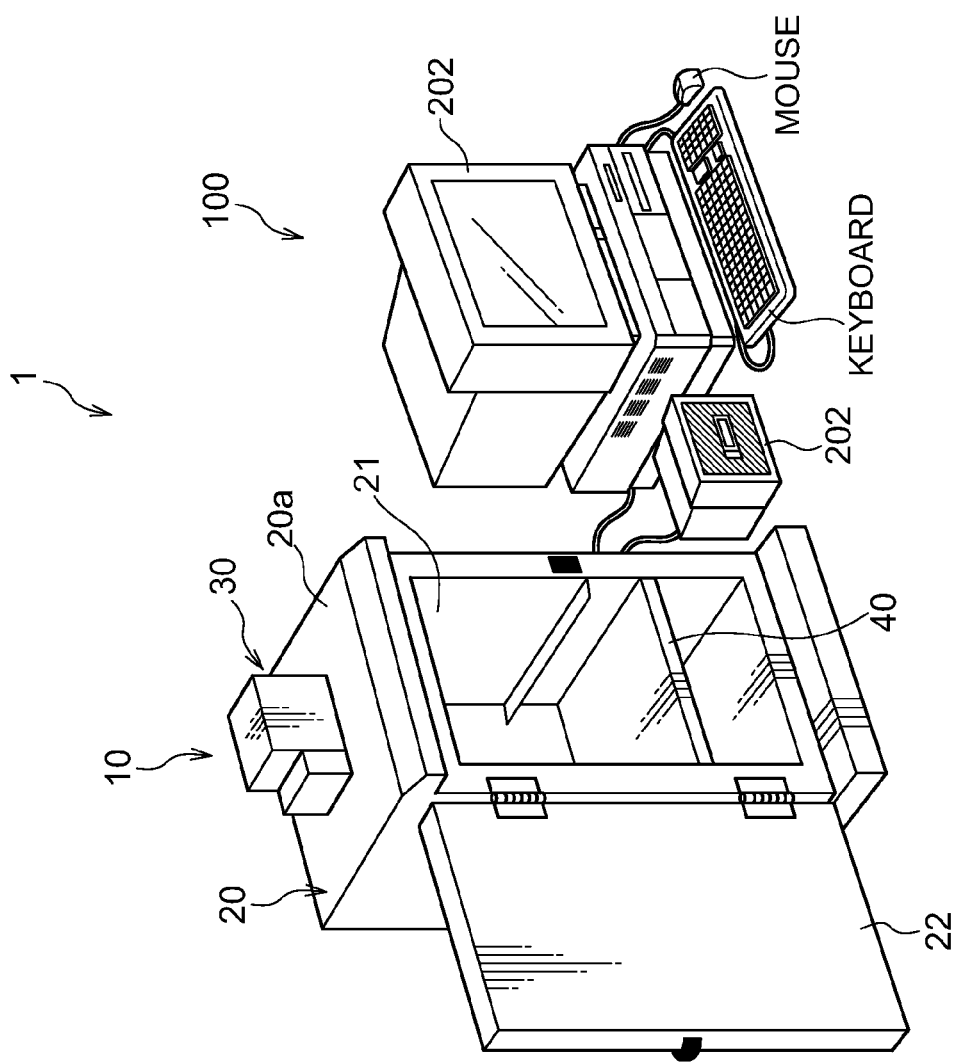
FIG. 1 is an overall perspective view of an imaging system including an imaging device according to an exemplary embodiment of the present invention.

FIG. 1 is a perspective view showing an example of an imaging system that uses an imaging device relating to the present invention. An imaging system 1 is an imaging system that, depending on the subject, images a subject without illuminating excitation light or by illuminating excitation light, and acquires a captured image of the subject. The imaging system 1 is configured including an imaging device 10 and an image processing device 100.

The imaging device 10 outputs, to the image processing device 100, image data of the subject that is obtained by imaging the subject. The image processing device 100 subjects the received image data to predetermined image processing as required, and displays the image data on a display 202.

In the present exemplary embodiment, the subject is a specimen colored with a fluorescent stain (fluorescent light emitting substance) rather than a chemical light emitting specimen, and the specimen is illuminated with excitation light and fluorescent light emitted from the specimen is detected.

Figure 2:
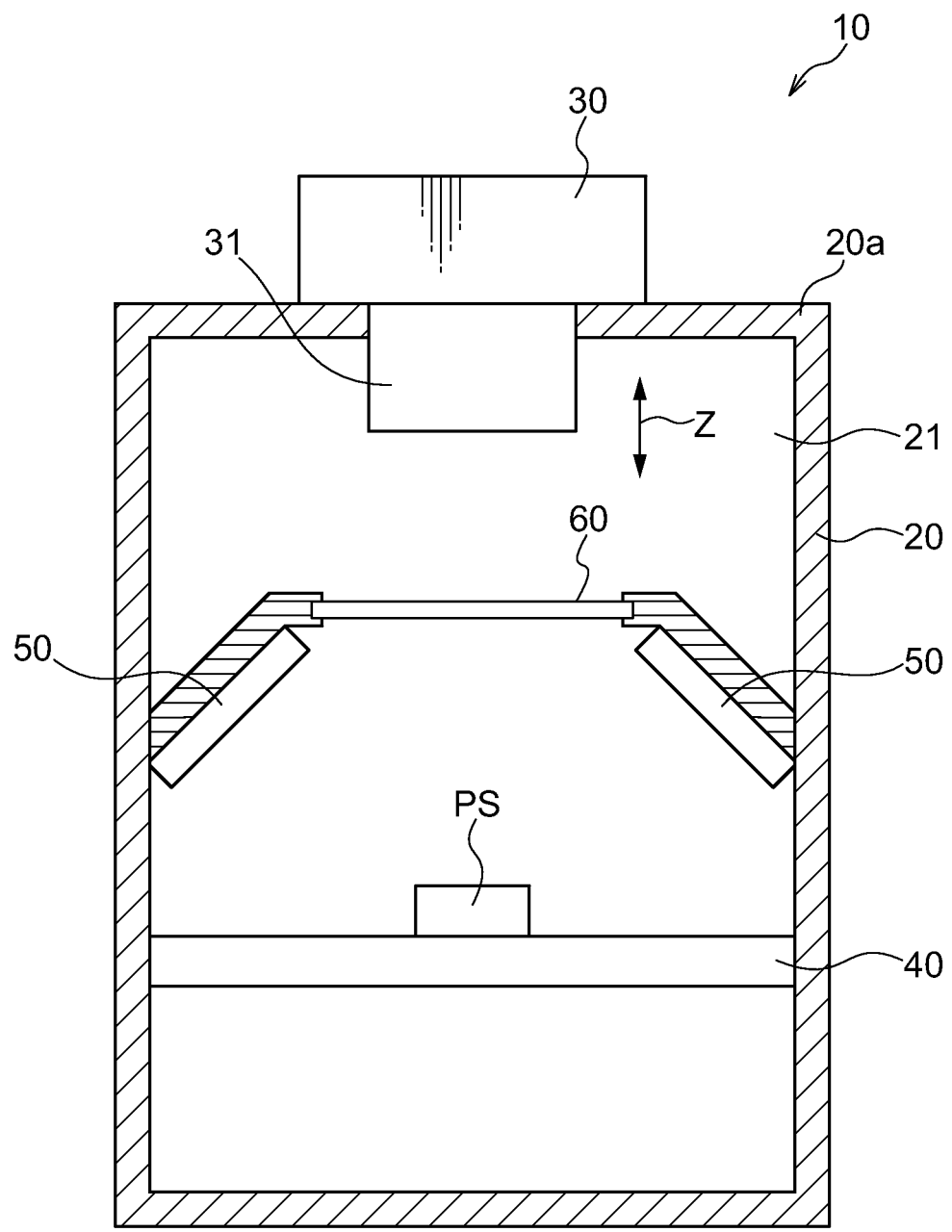
FIG. 2 is a face-on cross-section of an imaging device according to an exemplary embodiment of the present invention.

FIG. 2 illustrates the imaging device 10 from face-on, with a door 22 (see FIG. 1) of the imaging device 10 in an open state. As illustrated in FIG. 2, the imaging device 10 includes a subject placement section 40 for placing a subject PS, a casing 20 housing the subject placement section 40 inside, an imaging section 30, and an illumination light source 50 disposed inside the casing 20 for illuminating excitation light onto the subject PS.

The casing 20 includes a hollow section 21 formed in a substantially rectangular box shape. The door 22 illustrated in FIG. 1 is attached to the casing 20 so as to be opened and closed. A user opens the door 22 and places the subject PS inside the casing 20. The casing 20 is a dark box such that external light does not enter into the hollow section 21.

The imaging section 30 is configured including an imaging device fixed to a top face 20a of the casing 20, such as a CCD. Configuration may be made with a cooling mechanism attached to the imaging device, such as for example a Peltier device, to enable noise from dark current in captured image data is to be a great extent prevented by cooling the imaging device.

A imaging lens 31 is attached to the imaging section 30, and the imaging lens 31 is provided with a helicoid mechanism for focusing on the subject PS, and/or the imaging lens 31 is itself provided so as to be moveable in the arrow Z direction.

The illumination light source 50 is disposed above the subject placement section 40, as described later, and illuminates excitation light towards the subject PS. When imaging a fluorescent light emitting specimen as the subject PS, excitation light corresponding to the fluorescent stain of the subject is illuminated from the illumination light source 50 onto the subject.

Figure 3:
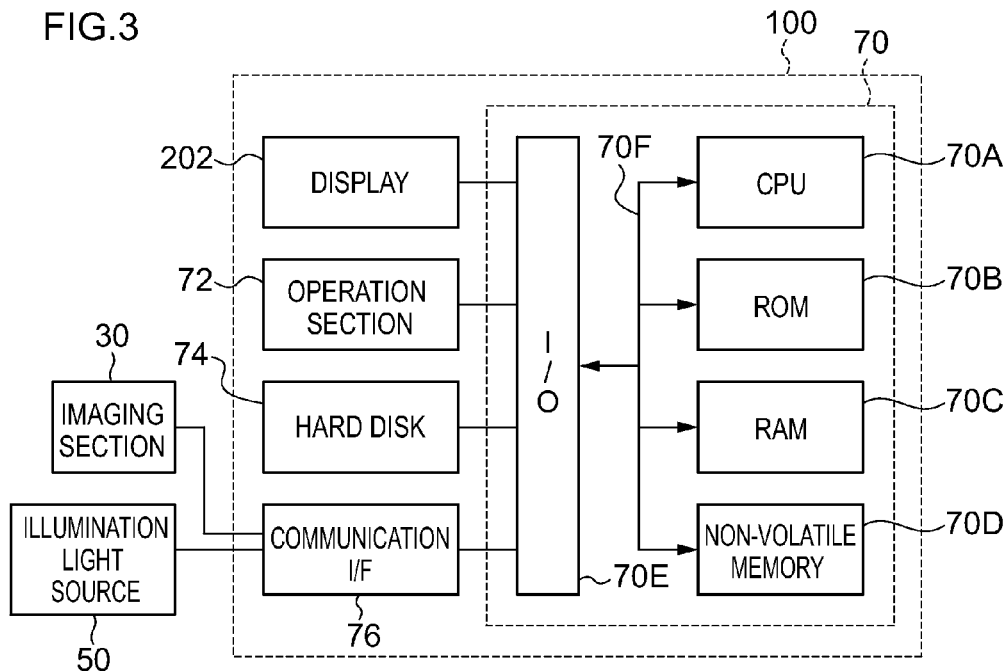
FIG. 3 is a block diagram illustrating an overall imaging device according to an exemplary embodiment of the present invention.

The image processing device 100 illustrated in FIG. 3 is a configuration including a main controller 70.

The main controller 70 is configured by a CPU (Central Processing Unit) 70A, a ROM (Read Only Memory) 70B, a RAM (Random Access Memory) 70C, a non-volatile memory 70D and an input/output interface (I/O) 70E connected to each other via a bus 70F.

The display 202, an operation section 72, a hard disk 74, and a communication I/F 76 are connected to the I/O 70E. The main controller 70 coordinates control of each functional section.

The display 202 is configured including, for example, a CRT or a liquid crystal display device, displays images captured by the imaging device 10, and displays for example screens for carrying out various types of setting and instruction on the imaging device 10.

The operation section 72 is configured including a mouse and a keyboard, and is employed by a user to give various types of instruction to the imaging device 10 by operating the operation section 72.

The hard disk 74 is stored with image data captured by the imaging device 10, with a control program for a control routine and an image processing program, described later, and various types of data such as table data.

The communication I/F 76 is connected to the imaging section 30 and to the illumination light source 50 of the imaging device 10. The CPU 70A, through the communication I/F 76: instructs the imaging section 30 to capture an image with imaging conditions corresponding to the type of subject; instructs the illumination light source 50 to illuminate excitation light when excitation light is to be illuminated onto the subject; receives data of images captured by the imaging section 30; and performs image processing, for example, on the received data.

Figure 4:
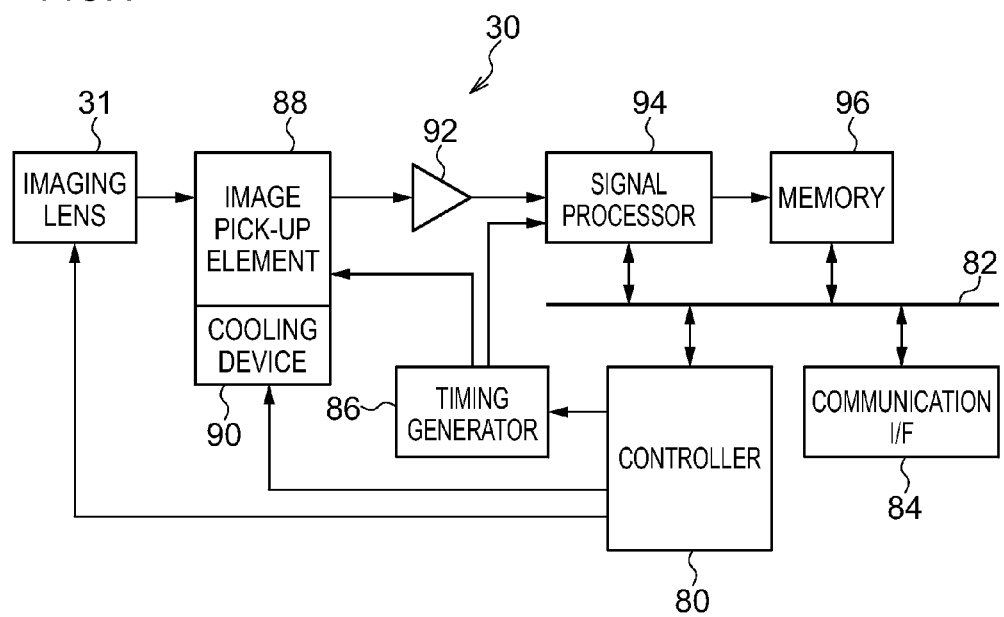
FIG. 4 is a block diagram illustrating the imaging section of the imaging device illustrated in FIG. 3.

The schematic configuration of the imaging section 30 is shown in FIG. 4. As shown in FIG. 4, the imaging section 30 has a controller 80, and the controller 80 is connected to a communication interface (I/F) 84 via a bus 82. The communication I/F 84 is connected to the communication I/F 76 of the image processing device 100.

When image capturing is instructed from the image processing device 100 via the communication I/F 84, the controller 80 controls the respective sections in accordance with the contents of the instruction, and images the subject PS that is disposed on the subject placement section 40, and transmits the image data of the captured image to the image processing device 100 via the communication I/F 84.

The imaging lens 31, a timing generator 86, and a cooling device 90 for cooling an image pick-up element 88 are connected to the controller 80.

While not illustrated in the drawings, the imaging lens 31 is configured, for example, including such components as a lens set made up from plural optical lenses, an aperture adjustment mechanism, a zoom mechanism and an autofocus mechanism. The lens set is provided so as to be movable along the arrow Z direction of FIG. 2 in order to focus on the subject PS and/or is provided with a helicoid mechanism. The aperture adjustment mechanism is a mechanism for changing the diameter of the aperture section so as to adjust the amount of light incident to the image pick-up element 88. The zoom mechanism is a mechanism for expanding or contracting the image capture range by adjusting the placement position of the lenses. The autofocus mechanism is a mechanism for adjusting the focus according to the separation distance between the subject PS and the imaging device 10.

As shown in FIG. 2, a portion of the light (fluorescent emission light) that has been given off by the subject PS under excitation by the excitation light emitted from the illumination light source 50 and that has passed through a detection filter 60 then passes through the imaging lens 31 and is focused as a subject image on the image pick-up element 88.

Although not illustrated, the image pick-up element 88 is configured to include light-receiving portions that each correspond to a respective pixel out of plural pixels, and matrixes for forwarding charges or signal voltage transmission. The image pick-up element 88 has the function of photoelectrically converting the subject image focused on the image pick-up face of the image pick-up element 88 into an electric signal. For example, an image sensor such as a charge coupled device (CCD), a metal oxide semiconductor (MOS) is used for the image pick-up element 88.

Explanation here is of a case in which the image pick-up element 88 is a CCD. The image pick-up element 88 is controlled by a timing signal from the timing generator 86, and photoelectrically-converts the incident light from the subject PS at each light-receiving portion.

The signal charge that has been photoelectrically-converted at the image pick-up element 88 is voltage-converted into an analog signal by a charge-voltage conversion amplifier 92, and output to a signal processor 94.

The timing generator 86 includes a resonator for generating a reference clock (system clock) for operating the imaging section 30, and, for example, the reference clock is supplied to each section, and the reference clock is divided to generate various timing signals. For example, timing signals are generated expressing a vertical synchronization signal, a horizontal synchronization signal and an electronic shutter pulse, and supplied to the image pick-up element 88. A sampling pulse for use in correlated double sampling (CDS) and a timing signal such as a conversion clock for use in analogue-digital conversion are generated and supplied to a signal processor 94.

The signal processor 94 is controlled by the timing signal from the timing generator 86, and is configured including a correlated double sampling (CDS) circuit that carries out correlated double sampling processing on the input analog signal, and an analog/digital (A/D) converter that converts the analog signal, on which the correlated double sampling processing was carried out, into a digital signal.

Correlated double sampling processing aims to reduce such features as noise included in the output signal of the image pick-up element 88, and is processing to obtain accurate image data by taking a difference between a feed-through component level included in the output signal of each single pick-up element (pixel) of the image pick-up element 88 and an image signal component level.

The analog signal, that has been subjected to the correlated double sampling processing by the CDS circuit, is converted into a digital signal by the A/D converter, and is output to and temporarily stored in the memory 96. The image data that is temporarily stored in the memory 96 is transmitted to the image processing device 100 via the communication I/F 84.

The cooling device 90 is, for example, configured by a Peltier device and controls according to a cooling temperature from the controller 80. Sometimes there is a detrimental effect on image quality due an increase in black current noise (thermal noise) of the image pick-up element 88 with increased temperature and exposure duration. The controller 80 therefore controls the cooling device 90 and cools the image pick-up element 88 based on a cooling temperature instructed from the image processing device 100.

Light Source (Illumination Light Source)

Figure 5:
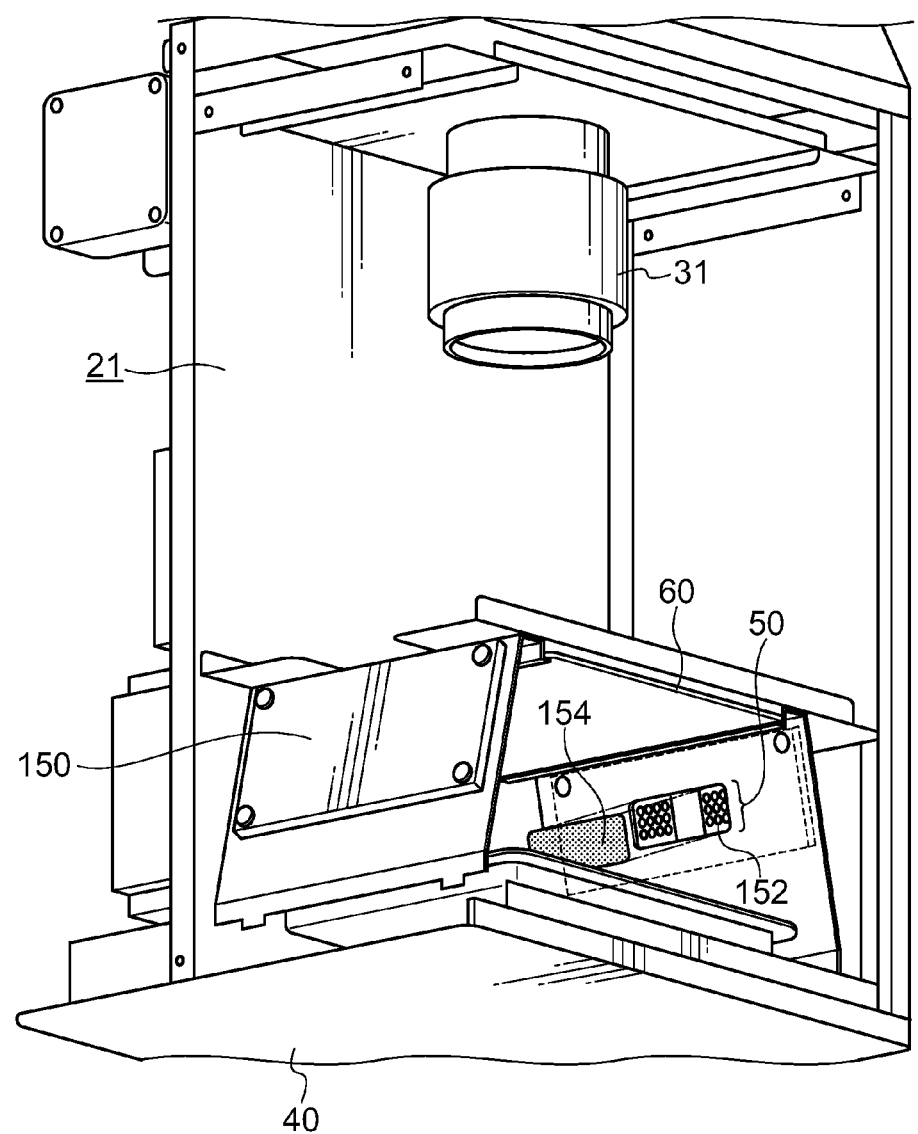
FIG. 5 is a perspective view illustrating an imaging device according to an exemplary embodiment of the present invention.

FIG. 5 shows an internal configuration of the hollow section 21 in the vicinity of the subject placement section 40. The illumination light source 50 positioned above the subject placement section 40 for illuminating excitation light onto the subject PS is configured as illustrated in FIG. 6B.

Figure 6A:
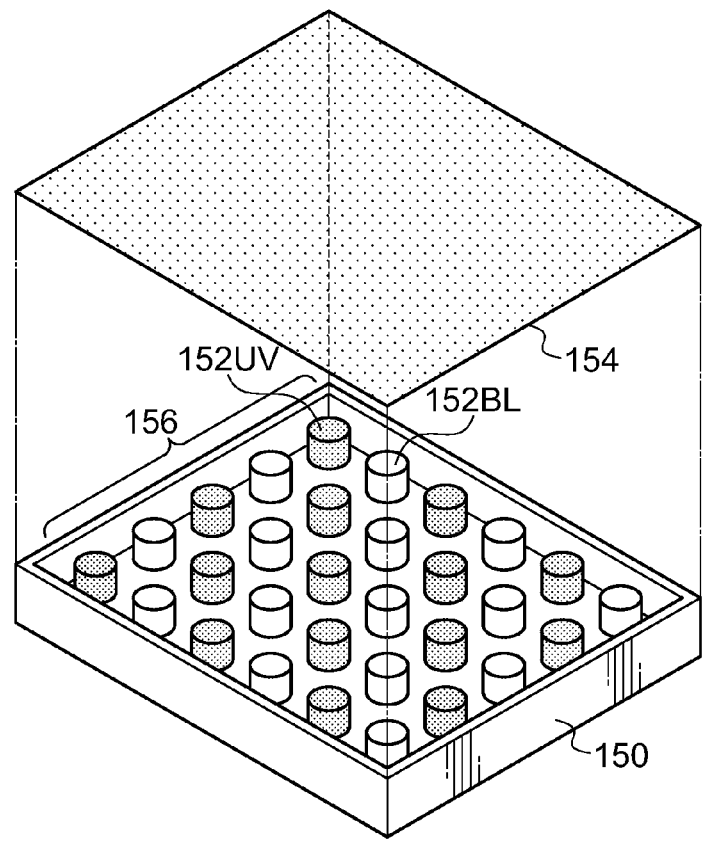
FIGS. 6A and 6B are perspective views illustrating an excitation light source of an imaging device according to an exemplary embodiment of the present invention.
Figure 6B:
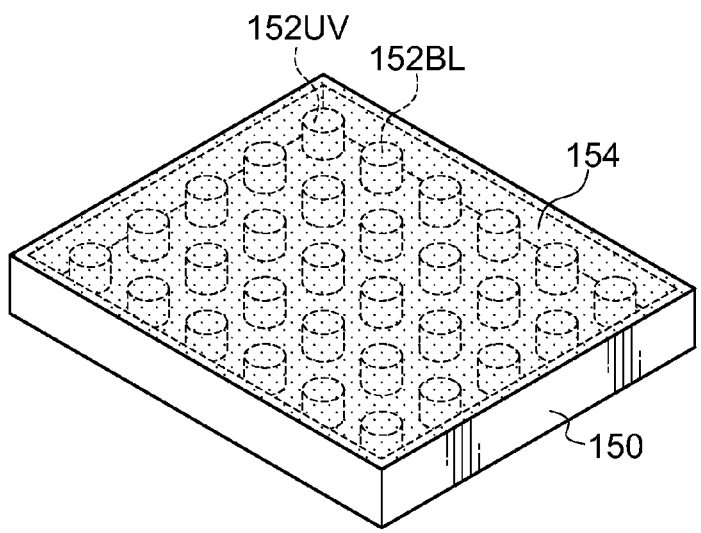

Namely, an LED array 156 (FIG. 6A) formed from LEDs 152 of at least two types having different principle wavelengths from each other is arrayed in two dimensions on a substrate 150 and covered by a single band pass filter 154 which transmits excitation light (FIG. 6B). The LEDs of different principle wavelengths are referred to collectively as LEDs 152.

The LED array 156 is, for example, a two dimensional array configured from LEDs 152UV with a principle wavelength component mainly in the vicinity of 365 nm in the near ultraviolet region (200 to 380 nm), and LEDs 152BL having a principle wavelength component in the blue visible light region in the vicinity of 460 nm. The LEDs 152UV and the LEDs 152BL are disposed alternately within each row, or LEDs of the same type are staggered in adjacent rows. Light emitted from each of the LEDs 152UV and LEDs 152BL is transmitted through the band pass filter 154 provided as a single filter that is not specifically matched to the spectral characteristics of the individual types of LED 152, and is illuminated onto the subject PS. The LEDs 152UV may have a principle wavelength component of 312 nm, as required.

Configuration may be made to enable light to be emitted simultaneously from the LEDs 152UV and the LEDs 152BL, or light to be emitted independently from the LEDs 152UV or the LEDs 152BL.

The band pass filter 154 is a single filter, and there is no need to change over filters or light source units even when, for example, plural types of fluorescent stains are employed in the subjects PS which are changed over by the imaging technician.

In a conventional fluorometric assay apparatus such as that described above, the fluorometric assay apparatus imposes the unwanted burden on an operator (imaging technician) of changing over the light source unit and/or the excitation filter according to the fluorescent stain employed.

Figure 7A:
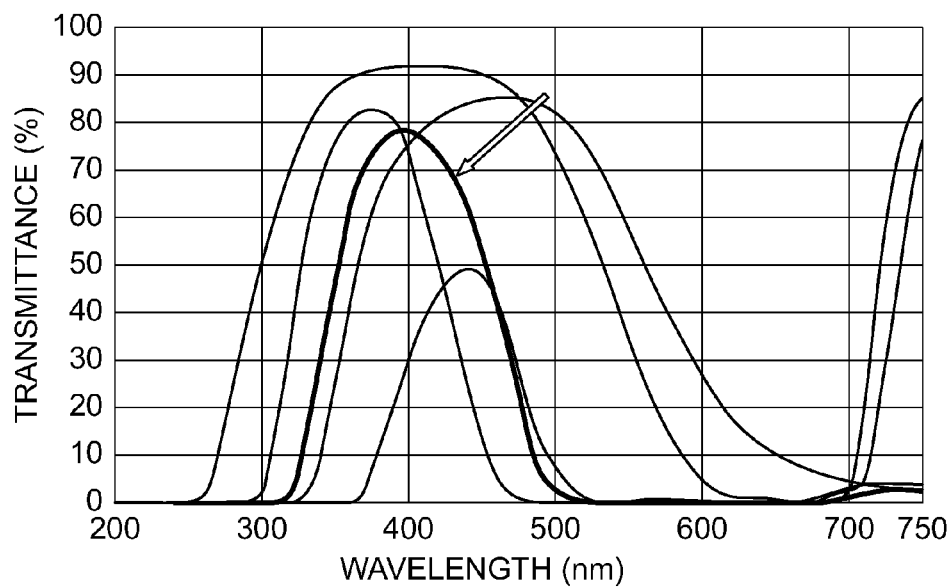
FIGS. 7A and 7B are graphs illustrating the spectral transmittance of a typical blue band pass filter and an ultraviolet transmission filter.

For example, conventionally, a blue band pass filter with the spectral transmittance as illustrated in FIG. 7A (white arrow) is employed when it is desired to let a light in a blue region pass through and cut lights having wavelengths of 500 nm or longer, and only blue light is illuminated onto the subject PS.

Figure 7B:
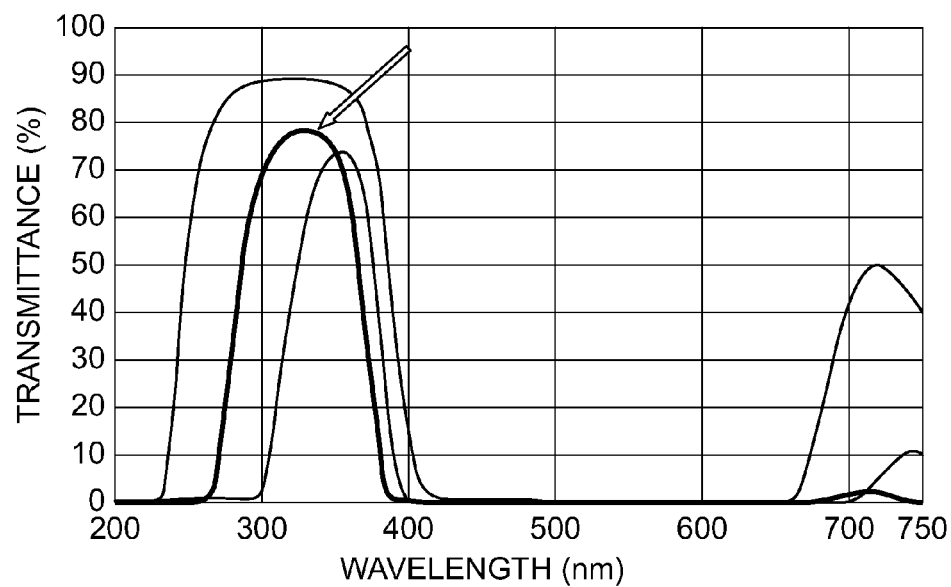

Additionally, an ultraviolet transmitting filter with the spectral transmittance as illustrated in FIG. 7B (white arrow) is employed when it is desired to let a light in an ultraviolet region pass through and cut lights having wavelengths of 400 nm or longer, and only the ultraviolet light is illuminated onto the subject PS.

In contrast thereto, the present exemplary embodiment employs the two dimensional array of LEDs 152UV with a principle wavelength component in the ultraviolet region and the LEDs 152BL with a principle wavelength component in the blue visible light region, thereby enabling illumination respectively in an ultraviolet region and/or a blue region.

Configuration may also be made with three or more types of LED arrayed on the substrate 150 so as to correspond to a greater number of types of fluorescent stain, or a configuration may be employed with a combination of different visible light emitting LEDs, or a combination of different ultraviolet emitting LEDs. Thereby, by suitably selecting the band pass filter 154 it becomes unnecessary to change over filters even in cases where a combination of plural fluorescent stains of different absorption wavelengths are employed.

The exemplary embodiment is configured with a single band pass filter 154 serving as an excitation filter disposed above the light source (the LED array 156), with the band pass filter 154 cutting out light having wavelengths of 300 nm or shorter and wavelengths of 500 nm or longer, and letting light having wavelengths more than 300 and less than 500 nm pass through.

Explanation follows of a case in which the typical DNA detection fluorescent stains ethidium bromide (EtBr) and SYBR Green are employed.

Figure 10:
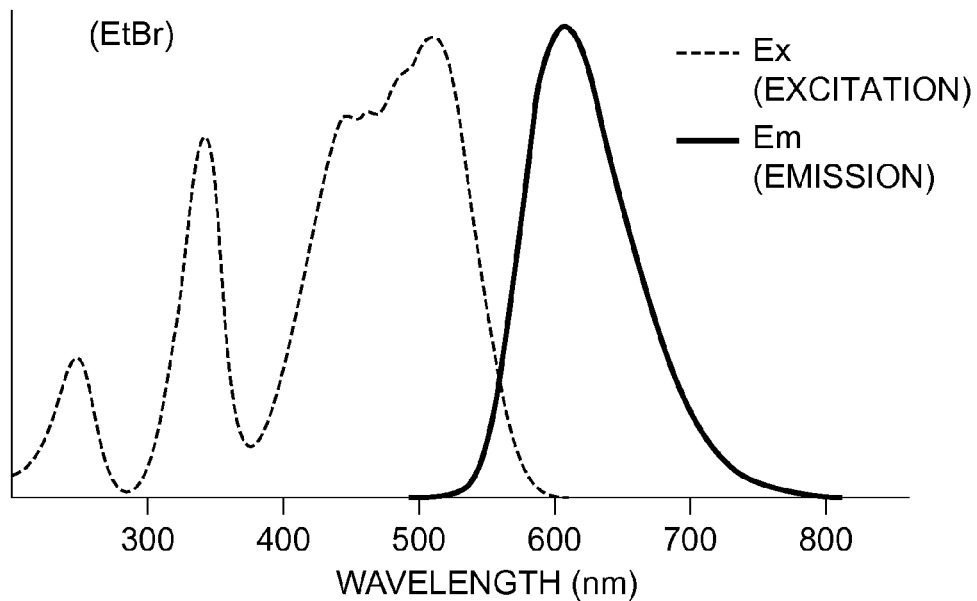
FIG. 10 is a graph illustrating the spectral characteristics of absorption and fluorescence of ethidium bromide (EtBr)

As shown in FIG. 10, while the absorption spectrum (fluorescence excitation spectrum) of EtBr has a peak in the vicinity of 500 nm, there is also a peak present in the ultraviolet region in the vicinity of 300 to 370 nm. The band pass filter 154 lets light having wavelengths more than 300 and less than 500 nm pass through, and so light from the LEDs 152UV with a principle wavelength component in the ultraviolet region is transmitted through the band pass filter 154, and a subject PS stained with EtBr is excited.

Figure 11:
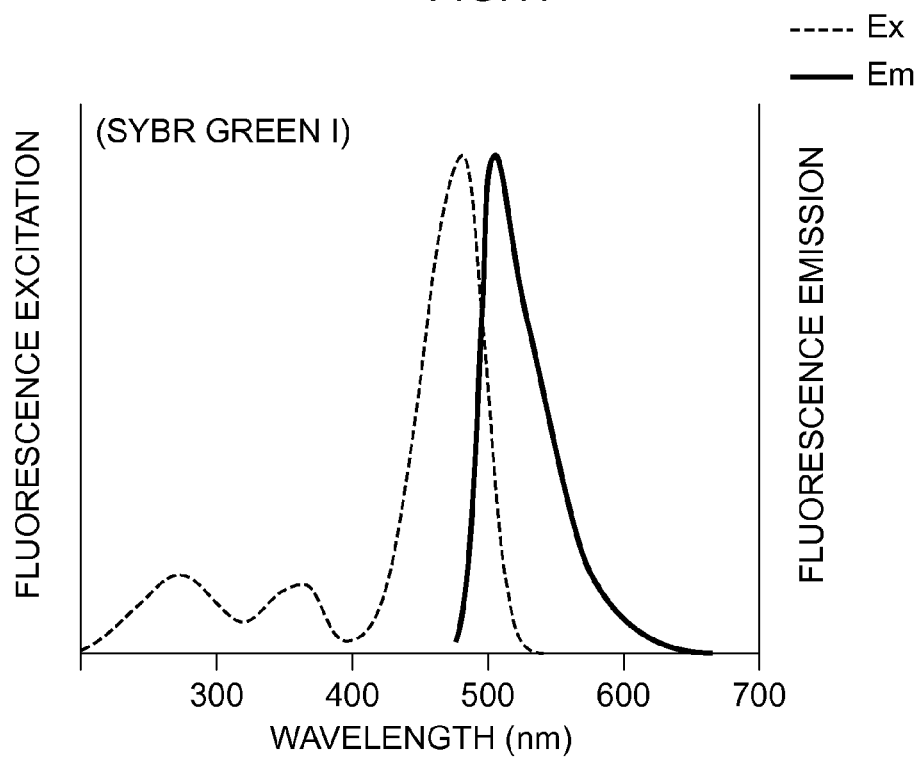
FIG. 11 is a graph illustrating the spectral characteristics of absorption and fluorescence of SYBR Green.

As shown in FIG. 11, the absorption spectrum of SYBR Green has a peak in the vicinity of 500 nm, however there is also a peak present in an ultraviolet to blue region in the vicinity of 300 to 400 nm. The band pass filter 154 lets light having wavelengths more than 300 and less than 500 nm pass through, and so light from the LEDs 152BL with a principle wavelength component in the blue region is transmitted through the band pass filter 154 and a subject PS stained with SYBR Green is excited.

It is accordingly possible to excite using the single illumination light source 50 in both cases of imaging specimens stained with EtBr and specimens stained with SYBR Green, and changing over of the illumination light source 50 is eliminated even when there is a switch in fluorescent stain type between EtBr and SYBR Green with respect to the specimens.

Since a configuration using the single band pass filter 154 disposed as the excitation filter above the LED array 156 is employed, both the LEDs 152UV with a principle wavelength component in the ultraviolet region and LEDs 152BL having a principle wavelength component in the blue region can be illuminated at the same time. Since the ultraviolet filters in particular are more costly than visible light filters, a lower cost illumination light source 50 can be provided by employing the single band pass filter 154 such as in the present exemplary embodiment.

As shown in FIG. 10, the fluorescent light emitted by EtBr is orange light of 500 nm or longer, with a peak around 590 nm, and as shown in FIG. 11, the fluorescent light emitted by SYBR Green is green light of 490 nm or longer, with a peak at about 530 nm. From the light emitted from the light source, the ranges of wavelengths therein that are the same as the above fluorescent emission light peaks are removed in advance by the band pass filter 154. This accordingly enables only the fluorescent light emitted by the fluorescent stain to be detected, without light from the illumination light source 50 of the same wavelength as the peaks of fluorescent emission light mixing with the fluorescent emission light itself which is emitted from the specimen.

Similarly, in an example in which ethidium bromide (EtBr) and SYBR Safe are employed as fluorescent stains, the absorption spectrum (fluorescence excitation spectrum) of EtBr, as explained above, has a peak in the ultraviolet region in the vicinity of 300 to 370 nm (FIG. 10). The band pass filter 154 lets light having wavelengths more than 300 and less than 500 nm pass through, and so light from the LEDs 152UV with a principle wavelength component in the ultraviolet region passes through the band pass filter 154 such that a subject PS stained with EtBr is excited.

Figure 12:
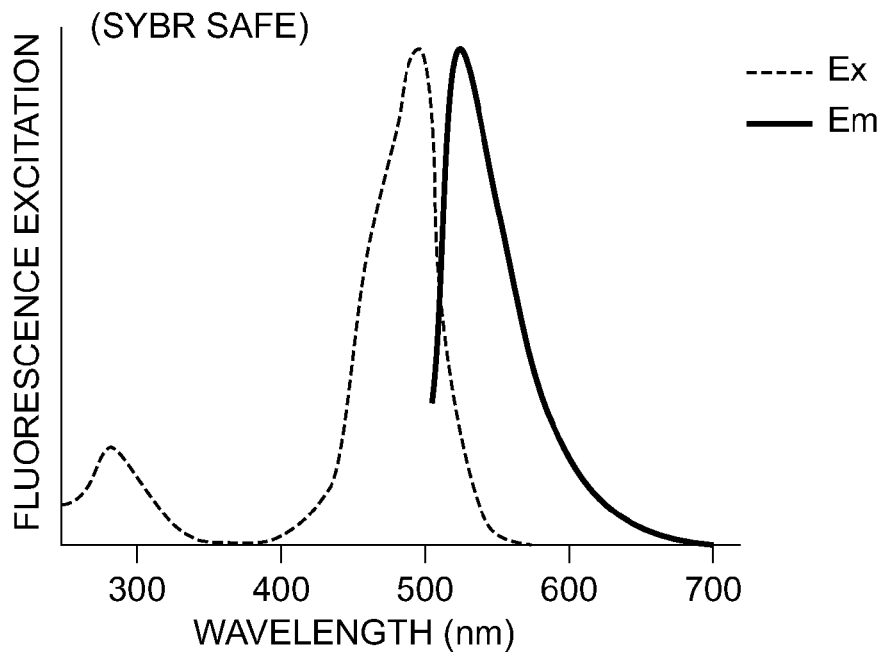
FIG. 12 is a graph illustrating the spectral characteristics of absorption and fluorescence of SYBR Safe.

As shown in FIG. 12, the absorption spectrum of SYBR Safe has a peak in the vicinity of 500 nm, however there is also a peak present in the ultraviolet region in the vicinity of 300 nm. The band pass filter 154 lets light having wavelengths more than 300 and less than 500 nm pass through, and so light from the LEDs 152UV having a principle wavelength component in the ultraviolet region is transmitted through the band pass filter 154 such that a subject PS stained with SYBR Safe is excited.

It is accordingly possible to excite using the single illumination light source 50 in both cases of imaging specimens stained with EtBr and specimens stained with SYBR Safe, and changing over of the illumination light source 50 is eliminated even when there is a switch in fluorescent stain type between EtBr and SYBR Safe with respect to the specimens.

Figure 13:
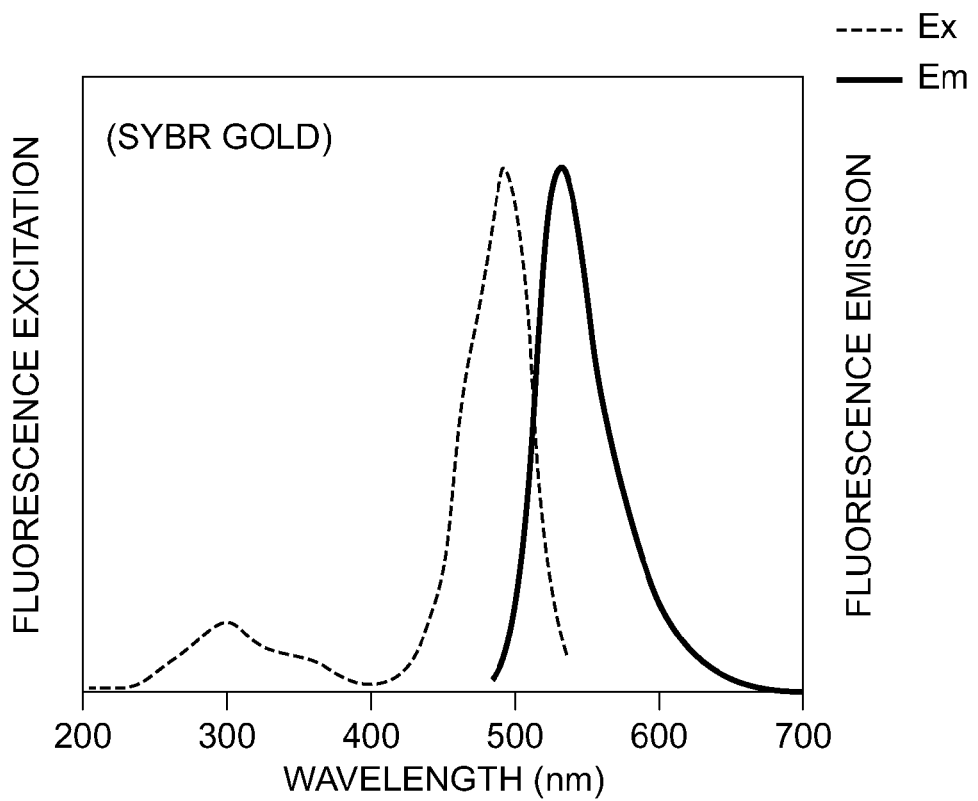
FIG. 13 is a graph illustrating the spectral characteristics of absorption and fluorescence of SYBR Gold.

Furthermore, in cases in which SYBR Gold with the excitation and fluorescent emission light characteristics illustrated in FIG. 13 and EtBr are employed as fluorescent stains, SYBR Gold has an absorption spectrum with a peak in the vicinity of 500 nm, however there is also a peak present in the ultraviolet region in the vicinity of 300 nm. The band pass filter 154 lets light having wavelengths more than 300 and less than 500 nm pass through, and so light from the LEDs 152UV having a principle wavelength component in the ultraviolet region passes through the band pass filter 154 such that a subject PS stained with SYBR Gold is excited.

It is accordingly possible to excite using the single illumination light source 50 for both cases of imaging specimens stained with EtBr and specimens stained with SYBR Gold, and changing over of the illumination light source 50 is eliminated even when there is a switch in fluorescent stain type between EtBr and SYBR Gold with respect to the specimens.

Detection Filter

In the present exemplary embodiment, as shown in FIG. 2 and FIG. 5, the detection filter 60 (fluorescent emission light filter) that lets light having wavelengths of 520 nm or longer pass through and cuts out light having shorter wavelengths, is disposed as a single filter in front of the imaging lens. In the present exemplary embodiment, a low cost orange tinted acrylic board is employed, however there are no particular limitations thereto, and another materials with suitable cutoff wavelengths such as optical glass may be employed.

Figure 9:
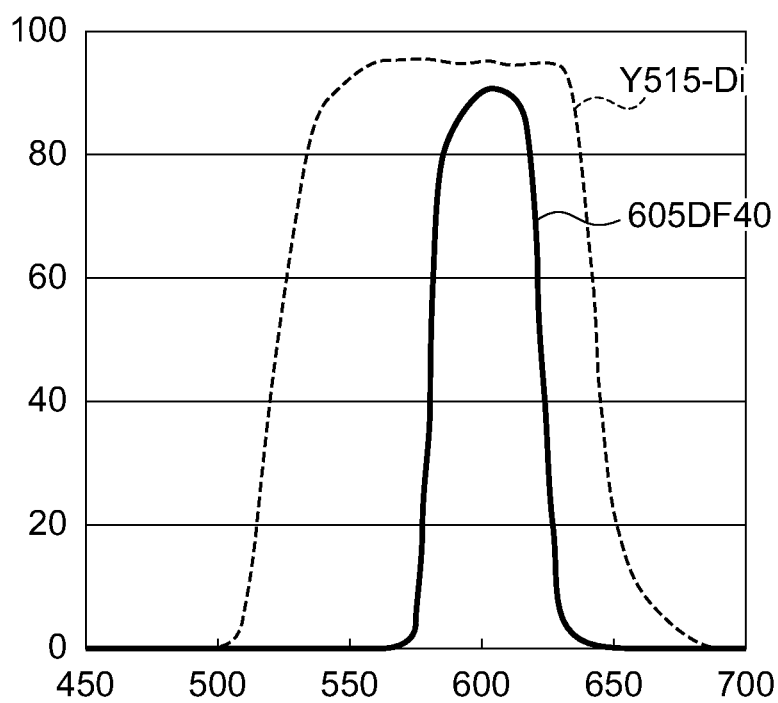
FIG. 9 is a graph illustrating the spectral transmittance of a related filter for detection.

There was previously a need to appropriately select a detection filter with spectral characteristics suited to each fluorescent stain as illustrated in FIG. 9, and detection filters needed to be changed over when the fluorescent stain was changed.

Namely when EtBr was being used for the fluorescent stain, a configuration was adopted in which a filter with the spectral characteristics as illustrated for 605DF40 of FIG. 9 was employed, so as to cut out the excitation light and let fluorescent emission light with a peak in the vicinity of 600 nm pass through and be guided to the imaging lens.

However, when SYBR Green was being used for the fluorescent stain, a configuration was adopted in which a filter with the spectral characteristics as illustrated for Y515-Di of FIG. 9 was employed, so as to cut out the excitation light and let fluorescent emission light with a peak in the vicinity of 550 nm to 650 nm pass through and be guided to the imaging lens. In such cases, since the peak of the excitation light is 500 nm, a particular filter was required with a sharp cutoff for light having wavelengths of 500 nm or shorter to eliminate the influence on detection of excitation light. There was therefore a need to employ respective dedicated detection filters when two types of fluorescent stain were being selectively used, leading to an increased burden on an operative.

Figure 8:
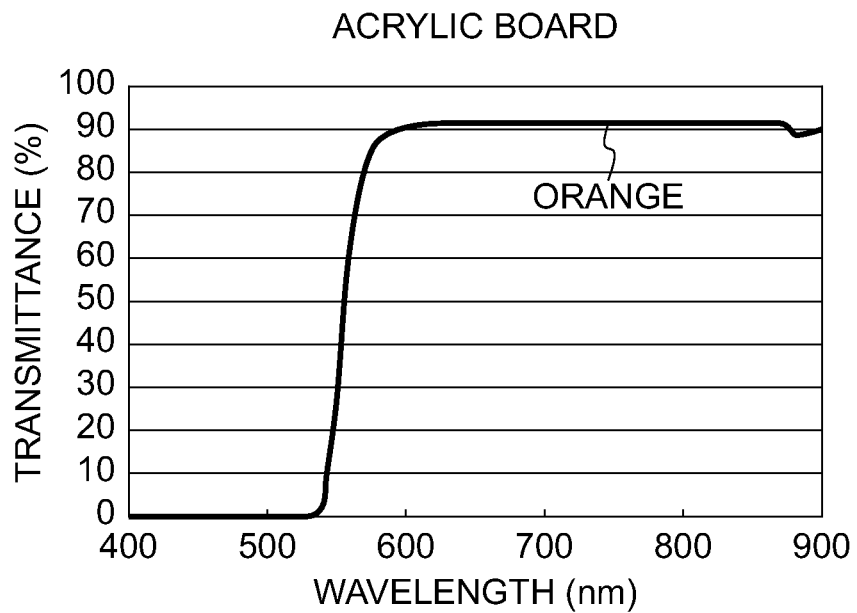
FIG. 8 is a graph illustrating the spectral transmittance of a long pass filter for detection according to an exemplary embodiment of the present invention.

In the present exemplary embodiment, since an orange tinted acrylic board is employed for the detection filter 60, light of wavelengths in the vicinity of 520 nm or longer passes through as shown in FIG. 8, and so a configuration is achieved in which the fluorescent emission light employed for detection passes through and is incident on the imaging lens 31 while still cutting out the influence of the excitation light by cutting out light of shorter wavelength than about 520 nm.

In the exemplary embodiments as explained above, the excitation light from the LED array 156 acting as the excitation light source passes through the band pass filter 154 acting as the single filter, and filtered light that acts as excitation light is illuminated onto the subject PS that has been stained with, for example, EtBr or SYBR Green. The excitation light that has passed through the band pass filter 154 is able to excite both EtBr and SYBR Green, thereby enabling detection to be performed without requiring such effort as the switching over of filters.

The light from the subject PS includes excitation light reflection components in addition to the fluorescent emission light required for detection, however only the fluorescent emission light required for detection is incident on the imaging lens 31 since excitation light in the ultraviolet region and the blue region has been removed by the detection filter 60.

When plural types of fluorescent stain are being selectively employed, an operative (imaging technician) is accordingly able to perform correct operation whichever fluorescent stain is employed, without needing to be aware of which fluorescent stain is being employed, and without performing changeover operations such as for the filter or light source unit.

Previously a case was possible in which a specimen using EtBr as the fluorescent stain was excited with UV with a principle wavelength of 312 nm or 365 nm, and detection was performed with an interference filter with central wavelength 605 nm and through-pass wavelength width of 40 nm, and then a specimen using SYBR Green as the fluorescent stain was excited with blue light with a principle wavelength of 460 nm, and detection was performed with long pass filter with 50% transmittance at 515 nm.

In contrast thereto, in the present exemplary embodiment, the LED array 156 with the two dimensional array of LEDs 152UV and LEDs 152BL as illustrated in FIG. 6 is employed as the light source, and, for example, a blue glass filter is employed with the spectral characteristics illustrated in FIG. 7A as the band pass filter 154, with the subjects PS excited by illuminating the LEDs 152UV and the LEDs 152BL at the same time.

As described above, a 3 mm thick orange tinted acrylic board with the transmittance spectrum as illustrated in FIG. 8 is employed as the detection filter 60, and when detection is performed, a test result is obtained in which it is possible to perform fluorescent emission light detection for EtBr and SYBR Green, either separately or both at the same time.

LED Color Separated Array

As shown in FIG. 6A and FIG. 6B, the LED array 156 having two dimensional array on the substrate 150 may, for example, be configured such that LEDs 152UV with a principle wavelength component in the ultraviolet region and LEDs 152BL having a principle wavelength component in the blue visible light region are disposed alternately within each row or the same type of LEDs are staggered in adjacent rows.

Figure 14:
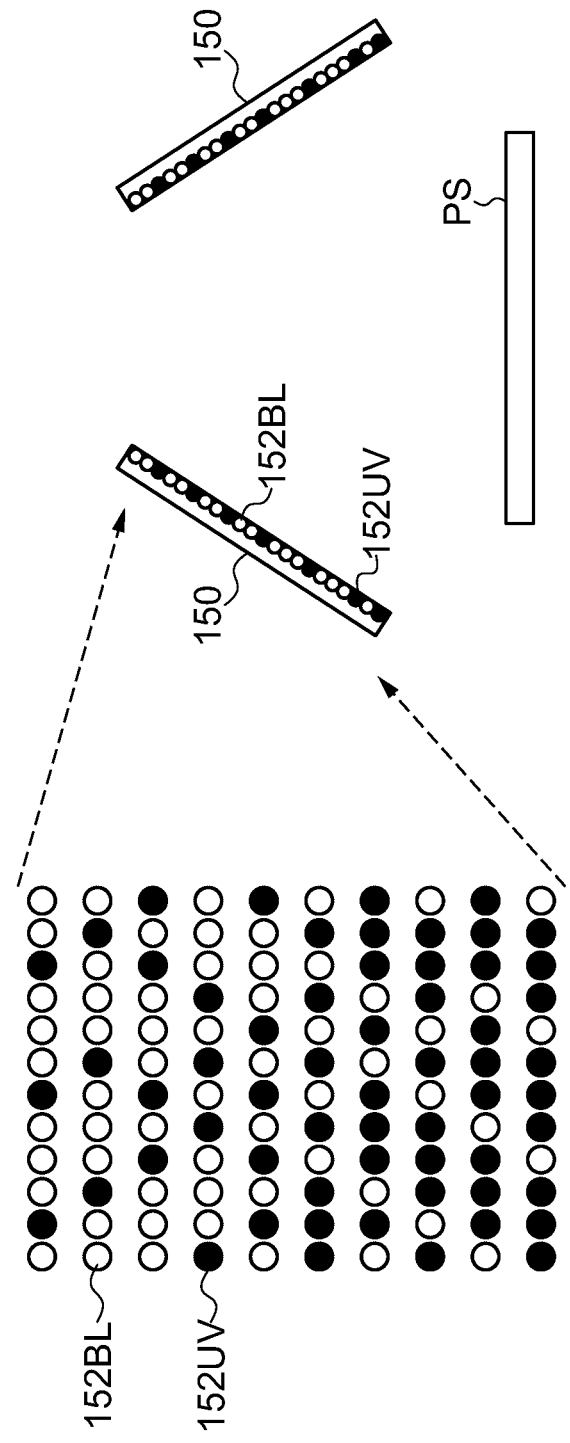
FIG. 14 is a schematic diagram illustrating a modified example of the excitation light source LED array shown in FIG. 6.

Configuration may be made such that the proportion of different types of LEDs 152 changes with the distance to the subject PS. Namely, as shown in FIG. 14, a configuration may be employed in which the proportion of the LEDs 152UV increases with vicinity to the subject PS (towards the bottom in FIG. 14).

Since generally the light intensity of ultraviolet LEDs is lower than that of visible LEDs, in the event that LEDs 152UV are disposed in the same proportion to the visible light LEDs, then the ultraviolet light intensity would be relatively insufficient. There is therefore a need to secure relatively higher ultraviolet light intensity in order to efficiently excite fluorescent stains with absorption peaks in the ultraviolet region.

In order to secure relatively higher ultraviolet light intensity, configuration on the substrate 150 may be made such that the number of individual LEDs 152UV is simply increased in the vicinity of the subject PS while the individual number of the LEDs 152BL is left unaltered. Alternatively the density of the LEDs 152UV in rows on the substrate may be increased with proximity to the subject PS. However, when such an approach is adopted, a non-standard substrate shape, such as a trapezoidal or triangular shape, is required, with this possibly leading to an increase in cost or manufacturing processes. However relatively higher ultraviolet light intensity can be secured without causing a deterioration in cost or space utilization by changing the proportions of the LEDs 152UV with respect to the LEDs 152BL within the two dimensional array of the LEDs 152 according to the separation distance from the subject PS as in the present exemplary embodiment.

Obviously consideration can be given to the shape of the substrate 150 and to the placement pattern of the LEDs, and configuration may be made in which most of the LEDs of low light intensity are disposed at the side nearest to the subject PS. The light intensity can also be secured by placing more low light intensity LEDs on the side nearest to the subject PS by employing a substrate with a shape such as a trapezoid or triangle shape as described above, and/or by employing a placement pattern such as one in which the row density of the LEDs 152 on the substrate increases with proximity to the subject PS.

Configuration may also be made such that the proportion of different types of LED on the substrate 150 varies with separation distance from the subject PS depending on the magnitude of light intensity within types of visible light emitting LED when ultraviolet LEDs are not employed, or depending on the magnitude of light intensity within types of ultraviolet light LED. Namely light intensity can be secured by placing an increasing number of individual lower light intensity LEDs nearer to the subject PS.

When three or more types of LED are arrayed on the substrate 150, light intensity can be similarly secured by disposing a greater number of the LEDs of low light intensity nearer to the subject PS.

As explained above, in the present exemplary embodiment, the following advantageous effects are exhibited due to light emitted from at least two types of LED disposed in a two dimensional array on a substrate passing through a single excitation filter.

The effort required by an operator to change over excitation filters or light source sections is eliminated, it is possible to excite plural fluorescent stains at lower cost, and the number of manufacturing processes can be reduced since there is no requirement to precisely match the illumination light intensity and directionality between each LED. Multi-stain fluorescent light detection at lower cost is also enabled by employing a single long pass filter in detection.

Multi-stain fluorescent light detection at lower cost is enabled by employing, as a single long pass detection filter, an orange transparent low cost tinted acrylic board for cutting wavelengths of 520 nm or shorter.

By disposing a two dimensional array of the near ultraviolet LEDs with a principle wavelength component at 312 nm or 365 nm and the blue LEDs with a principle wavelength component at 470 nm on a substrate, and by employing, as a single excitation filter, a band pass filter letting light within a band from near ultraviolet to blue pass through, the near ultraviolet LED can excite typical fluorescent stain EtBr and the blue LED can excite typical fluorescent stain SYBR Green. Thus, each type of fluorescent stain can be detected individually or the fluorescent stains can be detected at the same time as each other.

Other

While exemplary embodiments of the present invention have been described above the present invention is not limited by the above exemplary embodiments, and obviously various embodiments are possible with a scope not departing from the spirit of the present invention.

For example, an example has been given in which two types of LEDs 152 are configured as a two dimensional array on the same substrate 150, however there is no limitation thereto, and the present invention may be applied to a configuration employing three or more types of LED light source.

What is claimed is:

1. A fluorometric assay apparatus comprising:
   an LED light source configured with at least two types of excitation LED that have different principle wavelengths from each other and are disposed in a two dimensional array on a substrate;
   an imaging lens for imaging a subject;
   a single excitation filter provided between the LED light source and a subject, the single excitation filter transmitting each of principle wavelength components of the LED light source; and
   a single detection long pass filter provided between the imaging lens and the subject,
   wherein the at least two types of LED comprise a near ultraviolet LED with a principle wavelength component of 312 nm or 365 nm and a blue LED with a principle wavelength component of 470 nm, and the single excitation filter is a band pass filter that transmits light of a band from near ultraviolet to blue, and
   wherein the LED light source is configured by a two dimensional array disposed on a substrate such that the number of individual near ultraviolet LEDs per unit surface area of the substrate increases compared with the number of the blue LEDs as the separation distance between a surface area of the substrate and the subject gets shorter.

2. The fluorometric assay apparatus of claim 1, wherein the detection long pass filter is an orange tinted transparent acrylic board that cuts out light having wavelengths of 520 nm or shorter.

3. The fluorometric assay apparatus of claim 1 wherein the band pass filter cuts out light having wavelengths of 300 nm or shorter and cuts out light having wavelengths of 500 nm or longer and has a transmission peak in the vicinity of 400 nm.

4. The fluorometric assay apparatus of claim 1 wherein the band pass filter cuts out light having wavelengths of 260 nm or shorter and cuts out light having wavelengths of 400 nm or longer and has a transmission peak in the vicinity of 330 nm.

5. A fluorometric assay method comprising:
   exciting at least two types of fluorescent light emitting substance having different maximum absorption wavelengths to each other with an LED light source section configured with at least two types of excitation LED and a single excitation filter, the at least two types of excitation LED have different principle wavelengths from each other and are disposed in a two dimensional array on a substrate, and the single excitation filter covers the LEDs and transmits each of the principle wavelength components of the at least two types of excitation LED; and detecting fluorescent emission light that has been given off by the fluorescent light emitting substances and has passed through a single long pass filter provided as a detection filter between an imaging lens and a subject, wherein the at least two types of LED comprise a near ultraviolet LED with a principle wavelength component of 312 nm or 365 nm and a blue LED with a principle wavelength component of 470 nm, and the single excitation filter is a band pass filter that transmits light of a band from near ultraviolet to blue, and wherein the LED light source section is configured by a two dimensional array disposed on a substrate such that the number of individual near ultraviolet LEDs per unit surface area of the substrate increases compared with the number of the blue LEDs as the separation distance between a surface area of the substrate and the subject gets shorter.

6. The fluorometric assay method of claim 5 wherein the fluorescent light emitting substances are stained with EtBr and SYBR Green which are nucleic acid gel stains.

7. The fluorometric assay method of claim 5 wherein the fluorescent light emitting substances are stained with EtBr and SYBR Safe which are nucleic acid gel stains.

8. The fluorometric assay method of claim 5 wherein the fluorescent light emitting substances are stained with EtBr and SYBR Gold which are nucleic acid gel stains.

9. The fluorometric assay method of claim 5 wherein the at least two types of excitation LED with different principle wavelengths emit light at the same time as each other.

* * * * *